United States Patent [19]

Lachnit-Fixson et al.

[11] Patent Number: 4,621,079
[45] Date of Patent: Nov. 4, 1986

[54] MULTISTAGE COMBINATION PREPARATION AND ITS USE FOR ORAL CONTRACEPTION

[75] Inventors: Ursula Lachnit-Fixson; Renate Unger, both of Berlin, Fed. Rep. of Germany

[73] Assignee: Schering Aktiengesellschaft, Berlin and Bergkamen, Fed. Rep. of Germany

[21] Appl. No.: 685,016

[22] Filed: Dec. 21, 1984

[30] Foreign Application Priority Data

Dec. 22, 1983 [DE] Fed. Rep. of Germany ....... 3347125

[51] Int. Cl.⁴ ............................................. A61K 31/56
[52] U.S. Cl. ................................................... 514/170
[58] Field of Search ......................................... 514/170

[56] References Cited

U.S. PATENT DOCUMENTS 3,957,982  5/1976  Lachnit-Fixson .................. 514/170
4,544,554 10/1985  Pasquale ............................. 514/170

FOREIGN PATENT DOCUMENTS 0036229  9/1981  European Pat. Off. ........... 514/170

Primary Examiner—Elbert L. Roberts
Attorney, Agent, or Firm—Millen & White

[57] ABSTRACT

A multistage combination preparation is useful for oral contraception and comprises a surprisingly low amount of gestodene as the gestagen and comprises ethinylestradiol as the estrogen.

20 Claims, No Drawings

MULTISTAGE COMBINATION PREPARATION AND ITS USE FOR ORAL CONTRACEPTION

BACKGROUND OF THE INVENTION

This invention relates to a multistage combination preparation made up of 21 or 28 units, each to be administered on separate days, and its use for oral contraception for females of child bearing age.

Multistage combination preparations for oral contraception are known, for example, from DE-A No. 2,365,103 (U.S. Pat. No. 3,957,982) and the patents derived therefrom. Usually two or three stages are involved. These multistage preparations consist of 21 or 28 dragees, and contain, in the first stage, 4–6 dragees wherein each dragee contains an amount of estrogen corresponding to 0.02–0.05 mg of ethinylestradiol, and an amount of gestagen (progestogen) corresponding to 0.04–0.09 mg of d-norgestrel; in the second stage, (which can be a continuation of the first in essence), 4–6 dragees each containing onefold to twofold the amount of estrogen of the first stage, for example 0.03–0.05 mg of ethinylestradiol, and onefold to one and one-half-fold the amount of gestagen of the first stage, for example 0.05–0.125 mg of d-norgestrel; and, in the third stage, 9–11 dragees each containing an amount of estrogen that is larger than or exactly as large as that in the first stage and smaller than or exactly as large as in that in the second stage, for example, 0.025–0.050 mg of ethinylestradiol, and an amount of gestagen larger than that in the second stage, but no larger than three times as large as that in the first stage, for example 0.10–0.25 mg of d-norgestrel, and optionally, in the fourth stage, 7 dragees without estrogen and without gestagen. The number of dosage units in the three stages which contain estrogen and gestagen amounts to 21; to adapt to the 28-day cycle, 7 units free of active ingredient can be additionally included with the 21 units containing active agent.

Such multistage preparations provide higher compatibiltiy and improved cycle control as compared with the known combination preparations for cyclic or sequential usage.

European Patent Application No. 81200240 (publication No. 36229) describes a variant of a multistage preparation. This version is characterized in that the units of the first stage contain a higher amount of estrogen than the units of the subsequent stages.

In the multistage combination preparations, the estrogens can be utilized in amounts smaller than 0.05 mg of ethinylestradiol. Because of their staggered structures, the amounts of gestagen can likewise be kept at a low level. In this way, contraceptives are obtained using the lowest amounts of hormones thus practiced.

However, it is still desirable that the amount of gestagen be lowered still further.

SUMMARY OF THE INVENTION

It is an object of the invention to provide a new combination for oral contraception utilizing significantly lower amounts of gestagens.

It has now been found that the amount of gestagen in multistage combination preparations can be still further reduced by utilizing, as the gestagen, gestodene (17α-ethinyl-17β-hydroxy-18-methylestra-4,15-dien-3-one). Entirely unexpectedly, in spite of reduction of the gestagen dose, an excellent cycle control with good compatibility is attained. Contraceptive safety is ensured in all instances.

Accordingly, the present invention concerns a multistage combination preparation for oral contraception made up of 21 and/or 28 units of administration administration of one unit per day, wherein, in a first stage of 4–6 units, each unit contains an estrogen in a low dose and a gestagen in a low dose and, in a second stage of 4–6 units, each unit contains an estrogen with the same dose or a slightly raised dose, at most increased to twofold, and a gestagen with the same or a slightly raised dose, maximally increased to one and one-half-fold and, in a third stage of 9–11 units, each unit contains an estrogen with the same dose or a dose lowered again, maximally to the initial value, and a gestagen with a further raised dose, maximally to three times the initial value, and the three stages together consist of 21 units, optionally followed by seven further units without estrogen and without gestagen, characterized in that the gestagen is gestodene and the estrogen is ethinylestradiol, and the amount of ethinylestradiol in the first stage does not exceed 0.05 mg and of gestodene in the first stage does not exceed 0.07 mg.

The invention furthermore relates to the use of the multistage combination preparation for oral contraception. One unit of administration is given daily in the indicated stage sequence. The total number of days on which administration of the active agent combination takes place is to be in all cases 21, followed by 7 hormone-free days on which there are administered daily either 1 placebo or no units of administration. Gestodene is more active than d-norgestrel (U.S. Pat. No. 4,081,537) and the amount of gestodene can be lowered to values which are less than those of d-norgestrel, but in general lower amounts of gestagen cause problems with good compatibility.

DETAILED DESCRIPTION

The units of administration preferably contain, in the initial 4–6 days, 0.02–0.05 mg of ethinylestradiol and 0.04–0.07 mg of gestodene per unit. The amount of ethinylestradiol utilized according to this invention in the 4–6 days of the second stage preferably is per unit, 0.03–0.05 mg, and the amount of gestodene per unit is preferably 0.05–0.10 mg. The amount of ethinylestradiol utilized according to the invention in the 9–11 days of the third stage, per unit, is preferably 0.02–0.05 mg and the amount of gestodene per unit is preferably 0.08–0.12 mg.

Ethinylestradiol and gestodene are preferably administered orally in combination; however, they can also be administered separately and/or parenterally as a contemplated equivalent. Thus, the term "unit" herein contemplates both a single composition with the estrogens and gestagens admixed and also two separate ccompositions in a single unit, each one having one of the gestagen and the estrogen.

Ethinylestradiol and gestodene are processed, together with the additives, excipients and/or flavoring agents customary in galenic pharmacy, in accordance with the conventional methods into the usual forms of administration. For preferred oral administration, suitable are, in particular, tablets, dragees, capsules, pills, suspensions, or solutions. Such details are well known, see, e.g., U.S. Pat. No. 3,957,982, which disclosure is incorporated by reference herein entirely.

The 21 units of administration which contain active agent can be supplemented by 7 units of administration free of active agent (placebos) in order to bridge the days on which no hormones are to be administered. In this way, the habit of taking one unit per day is maintained. It is then merely necessary to continue, after 28 days (after withdrawal bleeding), with a new package of tablets.

The active agents can also be incorporated into film material as contemplated equivalents. By conventionally subdividing the film layer, units of administration can be made available with a corresponding dosage for buccal or sublingual administration. See, e.g., U.S. Pat. No. 4,136,162.

Accordingly, the invention also concerns pharmaceutical, packaged items (birth control kits) characterized by containing multistage combination preparations in 21 or 28 units of administration in a matched, fixedly determined sequence, the sequence corresponding to the stages of daily administration. The placebos and the units of administration of the three stages suitably differ in their color or shape.

The pharmaceutical package can be designed, inter alia, in the form of a see-through pack with, for example, 6 dragees of the first stage, 5 dragees of the second stage, 10 dragees of the third stage, and optionally 7 placebos, each of which is respectively removable daily, i.e. over 21 or 28 days.

In generally, the birth control combination and method of this invention are made and used conventionally, except as noted otherwise herein, e.g., analogously to the product.

The combination preparation of the invention is discussed primarily in terms of a three-stage regimen; however, all combinations and methods literally within the description are included, e.g., two stage versions wherein the amounts of gestagen and estrogen in "stages" one and two above are the same (Trinordiol ® and Perikursal ®).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Upon further study of the specification and appended claims, further objects and advantages of this invention will become apparent to those skilled in the art.

EXAMPLE 1

(Dragee Composition)

| | | |
|---|---|---|
| First Stage | 0.030 mg | Ethinylestradiol |
| (6 Dragees) | 0.050 mg | Gestodene |
| | 37.455 mg | Lactose |
| | 15.500 mg | Corn starch |
| | 0.065 mg | Calcium disodium edetate |
| | 1.700 mg | "Kollidon" 25 |
| | 0.200 mg | Magnesium stearate |
| | 55.000 mg | Total weight, supplemented to 90.000 mg with the usual sugar mixture and optionally coloring. |
| Second Stage | 0.040 mg | Ethinylestradiol |
| (5 Dragees) | 0.070 mg | Gestodene |
| | 37.425 mg | Lactose |
| | 15.500 mg | Corn starch |
| | 0.065 mg | Calcium disodium edetate |
| | 1.700 mg | "Kollidon" 25 |
| | 0.200 mg | Magnesium stearate |
| | 55.000 mg | Total weight, supplemented to 90.000 mg with the usual sugar mixture and optionally coloring. |
| Third Stage | 0.030 mg | Ethinylestradiol |
| (10 Dragees) | 0.100 mg | Gestodene |
| | 37.405 mg | Lactose |
| | 15.500 mg | Corn starch |
| | 0.065 mg | Calcium disodium edetate |
| | 1.700 mg | "Kollidon" 25 |
| | 0.200 mg | Magnesium stearate |
| | 55.000 mg | Total weight, supplemented to 90.000 mg with the usual sugar mixture and optionally coloring. |

EXAMPLE 2

(Dragee Composition)

| | | |
|---|---|---|
| First Stage | 0.030 mg | Ethinylestradiol |
| (11 Dragees) | 0.050 mg | Gestodene |
| | 37.455 mg | Lactose |
| | 15.500 mg | Corn starch |
| | 0.065 mg | Calcium disodium edetate |
| | 1.700 mg | "Kollidon" 25 |
| | 0.200 mg | Magnesium stearate |
| | 55.000 mg | Total weight, supplemented to 90.000 mg with the usual sugar mixture and optionally coloring. |
| Second Stage | 0.030 mg | Ethinylestradiol |
| (10 Dragees) | 0.100 mg | Gestodene |
| | 37.405 mg | Lactose |
| | 15.500 mg | Corn starch |
| | 0.065 mg | Calcium disodium edetate |
| | 1.700 mg | "Kollidon" 25 |
| | 0.200 mg | Magnesium stearate |
| | 55.000 mg | Total weight, supplemented to 90.000 mg with the usual sugar mixture and optionally coloring. |

EXAMPLE 3

(Film Composition)

First Stage
  11 units containing
    0.050 mg of gestodene
    0.030 mg of ethinyl-estradiol
Second Stage
  10 units containing
    0.100 mg of gestodene
    0.030 mg of ethinyl-estradiol
Third Stage
  7 units containing
    50.000 mg of iron(II)fumarate
Preparation for 1100 units, First Stage
  0.066 gram of food color yellow No. 2 (tartrazine; E 102) is dissolved in
    4.400 grams of water, and then introduced into
    86.900 grams of ethyl alcohol. In this solution are dissolved
    0.055 gram of gestodene,
    0.033 gram of ethinyl-estradiol and
    0.198 gram of polyoxyethylene-polyoxypropylene copolymer. Into this solution are introduced
    16.313 grams of hydroxypropyl-cellulose and
    16.313 grams of cellulose to form a homogeneous suspension.
Preparation for 1000 units, Second Stage 0.065 gram of food color orange No. 2 (Sunset Yellow; E 110) is dissolved in
4.000 grams of water, and then introduced into
79.000 grams of ethyl alcohol. In this solution are dissolved
0.100 gram of gestodene,
0.030 gram of ethinyl-estradiol and
0.180 gram of polyoxyethylene-polyoxypropylene copolymer. Into this solution are introduced
14.790 grams of hydroxypropyl-cellulose and
14.790 grams of cellulose to form a homogeneous suspension.

Preparation for 700 units, Third Stage
0.042 gram of saccharin,
0.042 gram of cream essence and
0.406 gram of polyoxyethylene-polyoxypropylene copolymer are dissolved in a mixture of
55.300 grams of ethyl alcohol and
2.800 grams of water. Into this solution are introduced
35.000 grams of iron(II)fumurate,
17.500 grams of hydroxypropyl-cellulose,
5.950 grams of cocoa and
4.060 grams of cellulose to form a homogeneous suspension.

The suspensions so prepared are drawn on a suitable film drawing apparatus having a three compartment doctor (width per compartment 18 mm) into a sheet and dried. By appropriate division, e.g., by perforation, there can be distributed over the width of the film three units of 18×18 mm for First Stage, of 18×19.8 mm for Second Stage and of 18×28 mm for Third Stage, each having different contents of active substance. There can be separated from the film web preparations having 11 units of First Stage, 10 units of Second Stage and 7 units of Third Stage.

Clinical Investigations on Compatibility and Contraceptive Safety.

The three-stage preparation according to Example 1 of the present invention (A) was compared with the three-stage preparation according to the example in German Pat. No. 2,365,103 (U.S. Pat. No. 3,957,982, example 2) (B).

Test preparation A was used for treating 377 women of childbearing age in 2,123 cycles, and test preparation B was used to treat 362 women of childbearing age in 2,088 cycles. Each of the women received daily one dragee for 21 days; the subsequent 7 days, during which withdrawal bleeding took place, were left without administering anything. This form of administration was retained over 6 cycles. Most of the women participated in the trial until the end.

No pregnancies occurred during the entire treatment period.

Both preparations were well compatible.

In case of three-stage preparation A, less intracyclic menstrual bleeding occurred than in case of three-stage preparation B.

| Cycle | | 1st | 3rd | 6th |
|---|---|---|---|---|
| Spotting | A | 11.8 | 7.4 | 3.1 |
| | B | 15.9 | 11.9 | 5.9 |
| Withdrawal | A | 2.0 | 1.5 | 0.9 |
| Bleeding | B | 0.9 | 0.9 | 0.9 |

| Cycle | | 1st | 3rd | 6th |
|---|---|---|---|---|
| Spotting and | A | 1.1 | 0.9 | 0.3 |
| Withdrawal Bleeding | B | 2.9 | 1.8 | 1.2 |

The good cycle control in the case of A is surprising since A has a lower dosage of the gestagen proportion than B.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A multiphase combination composition suitable for oral contraception comprising 21 separate dosage units suitable for daily administration of one dosage unit per day consisting essentially of
as a first phase 4–6 units comprising, in admixture with a pharmaceutically acceptable carrier, ethinylestradiol as estrogen in a low contraceptively effective dose of up to 0.05 mg and gestodene as gestagen in a low contraceptively effective dose of up to 0.07 mg;
as a second phase, 4–6 units comprising, in admixture with a pharmaceutically acceptable carrier, ethinylestradiol in the same dose or a higher dose than that of the first phase, up to twice the first-phase dose, and gestodene in the same or a higher dose than that of the first phase up to one and one-half that of the first-phase and,
as a third phase, 9–11 units comprising, in admixture with a pharmaceutically acceptable carrier, ethinylestradiol in the same dose or a lower dose than the second phase, as low as that of the first phase, and gestodene in a dose higher than that of the second phase, up to three times that of the first phase.

2. A composition of claim 1 further comprising, as a fourth stage, 7 separate placebo dosage units containing no estrogen and no gestagen.

3. A composition of claim 1 consisting of said 21 dosage units and no placebo units.

4. A composition of claim 1 wherein the dosage units of administration in the first stage contain 0.02–0.05 mg of ethinylestradiol and 0.04–0.07 mg of gestodene; in the second stage contain 0.03–0.05 mg of ethinylestradiol and 0.05–0.10 mg of gestodene; and in the third stage contain 0.02–0.05 mg of ethinylestradiol and 0.08–0.12 mg of gestodene.

5. A composition of claim 1, wherein the number of dosage units in the first stage is 6, in the second stage 5, and in the third stage 10.

6. A composition of claim 1 wherein the dosage units are tablets or dragees.

7. A composition of claim 1, wherein the first stage consists essentially of 6 dragees, each dragee containing about 0.03 mg of ethinylestradiol and about 0.05 mg of gestodene, the second stage consists essentially of 5 dragees, each dragee containing about 0.04 mg of ethinylestradiol and about 0.07 mg of gestodene, and the third stage consists essentially of 10 dragees, each dragee containing about 0.03 mg of ethinylestradiol and about 0.10 mg of gestodene.

8. A composition of claim 1 wherein the estrogen and the gestagen are mixed together in each dosage unit.

9. A composition of claim 1 wherein the dosage units are film layers.

10. A composition of claim 1 in the form of a kit comprising the 21 dosage units in a single package from which each is separately and independently removable.

11. A composition of claim 2 in the form of a kit comprising the 28 dosage units in a single package from which each is separately and independently removable.

12. A method of contraception which comprises administering for 21 successive days to a female of childbearing age, a combination of an estrogen and a gestagen, in the form of 21 separate dosage units, one per day, as a first phase 4–6 units comprising, in admixture with a pharmaceutically acceptable carrier, ethinylestradiol as estrogen in a low contraceptively effective dose of up to 0.05 mg and gestodene as gestagen in a low contraceptively effective dose of up to 0.07 mg;

as a second phase, 4–6 units comprising, in admixture with a pharmaceutically acceptable carrier, ethinylestradiol in the same dose or a higher dose than that of the first phase, up to twice the first-phase dose, and gestodene in the same or a higher dose than that of the first phase up to one and one-half that of the first-phase and, as a third phase, 9–11 units comprising, in admixture with a pharmaceutically acceptable carrier, ethinylestradiol in the same dose or a lower dose than the second phase, as low as that of the first phase, and gestodene in a dose higher than that of the second phase, up to three times that of the first phase, 13. A method of claim 12 wherein the units are administered orally.

14. A method of claim 13 further comprising, in a fourth stage, administering 7 separate placebo dosage units, one per day, for seven days, each containing no estrogen and no gestagen.

15. A method of claim 13 wherein for the 7 days after said 21 day period, no gestagen and no estrogen are administered.

16. A method of claim 13 wherein the dosage units of administration in the first stage contain 0.02–0.05 mg of ethinylestradiol and 0.04–0.07 mg of gestodene; in the second stage contain 0.03–0.05 mg of ethinylestradiol and 0.05–0.10 mg of gestodene; and in the third stage contain 0.02–0.05 mg of ethinylestradiol and 0.08–0.12 mg of gestodene.

17. A method of claim 13 wherein the number of dosage units in the first stage is 6, in the second stage 5, and in the third stage 10.

18. A method of claim 13 wherein the dosage units are tablets or dragees.

19. A method of claim 13 wherein the first stage consists essentially of 6 dragees, each dragee containing about 0.03 mg of ethinylestradiol and about 0.05 mg of gestodene, the second stage consists essentially of 5 dragees, each dragee containing about 0.04 mg of ethinylestradiol and about 0.07 mg of gestodene, and the third stage consists essentially of 10 dragees, each dragee containing about 0.03 mg of ethinylestradiol and about 0.10 mg of gestodene.

20. A method of claim 13 wherein the estrogen and the gestagen are mixed together in each dosage unit.

* * * * *